US008784427B2

(12) United States Patent
Fallin et al.

(10) Patent No.: US 8,784,427 B2
(45) Date of Patent: Jul. 22, 2014

(54) ORTHOPEDIC GUIDE AND METHOD

(75) Inventors: Thomas Wade Fallin, Hyde Park, UT (US); M. Mary Sinnott, Logan, UT (US); Patrick Michel White, West Chester, PA (US)

(73) Assignee: Smith & Nephew, Inc., Memphis, TN (US)

( * ) Notice: Subject to any disclaimer, the term of this patent is extended or adjusted under 35 U.S.C. 154(b) by 82 days.

(21) Appl. No.: 13/527,648

(22) Filed: Jun. 20, 2012

(65) Prior Publication Data
US 2013/0012952 A1   Jan. 10, 2013

Related U.S. Application Data

(60) Provisional application No. 61/568,137, filed on Dec. 7, 2011, provisional application No. 61/505,992, filed on Jul. 8, 2011, provisional application No. 61/506,000, filed on Jul. 8, 2011, provisional application No. 61/506,004, filed on Jul. 8, 2011.

(51) Int. Cl.
A61B 17/58    (2006.01)
A61B 17/60    (2006.01)
A61F 2/00     (2006.01)

(52) U.S. Cl.
USPC ............... 606/96; 606/103; 606/104

(58) Field of Classification Search
USPC .......... 606/96–99, 103, 104, 86 R, 87
See application file for complete search history.

(56) References Cited

U.S. PATENT DOCUMENTS

| 2,301,500 | A | 11/1942 | Anderson |
| 2,697,433 | A | 12/1954 | Zehnder |
| 4,686,972 | A | 8/1987 | Kurland |
| 4,739,751 | A | 4/1988 | Sapega et al. |
| 4,781,182 | A | 11/1988 | Purnell et al. |
| 4,823,780 | A | 4/1989 | Odensten et al. |
| 4,883,048 | A | 11/1989 | Purnell et al. |
| 4,964,861 | A | 10/1990 | Agee et al. |
| 5,112,335 | A | 5/1992 | Laboureau et al. |
| 5,112,337 | A | 5/1992 | Paulos et al. |
| 5,520,693 | A | 5/1996 | McGuire et al. |
| 5,968,050 | A | 10/1999 | Torrie |
| 6,187,011 | B1 | 2/2001 | Torrie |
| 6,725,082 | B2 | 4/2004 | Sati et al. |
| 6,878,150 | B1 | 4/2005 | McGuire et al. |
| 7,025,770 | B2 | 4/2006 | McGuire et al. |
| 7,575,578 | B2 | 8/2009 | Wetzler et al. |
| 8,110,000 | B2 | 2/2012 | Collins |
| 8,277,459 | B2 * | 10/2012 | Sand et al. ............ 606/96 |
| 8,409,225 | B2 | 4/2013 | Bull |
| 8,449,552 | B2 | 5/2013 | Sanders |
| 8,551,123 | B2 | 10/2013 | Pandya |
| 2007/0233128 | A1 | 10/2007 | Schmieding et al. |

(Continued)

OTHER PUBLICATIONS

Blitz, et al. "Plantar Plate Repair of the Second Metatarsophalangeal Joint: Technique and Tips" Journal of Foot & Ankle Surgery, 2004 43(4):266-270.

(Continued)

*Primary Examiner* — Andrew Yang
(74) *Attorney, Agent, or Firm* — David A. Chambers; David A. Warmbold

(57) ABSTRACT

A guide and method for cutting bones adjacent a joint at locations referenced to the joint anatomy is presented.

14 Claims, 16 Drawing Sheets

(56) References Cited

U.S. PATENT DOCUMENTS

| | | |
|---|---|---|
| 2009/0171355 A1* | 7/2009 | Amis et al. .................... 606/53 |
| 2011/0009867 A1 | 1/2011 | Oren |
| 2011/0144647 A1 | 6/2011 | Appendzeller et al. |
| 2011/0208198 A1 | 8/2011 | Anderson et al. |

OTHER PUBLICATIONS

Coughlin, et al. "Second MTP Joint Instability: Grading of the Deformity and Description of Surgical Repair of Capsular Insufficiency" The Physician and Sportmedicine, Sep. 3, 2011, 39(3):132-141.

Fleming and Camasta, "Plantar Plate Dysfunction" Chapter 4, (2002) pp. 22-28, http://www.podiatryinstitute.com/pdfs/Update_2002/2002_04.pdf.

Gregg et al., "Plantar Plate Repair and Weil Osteotomy for Metatarsophalangeal Joint Instability" Foot and Ankle Surgery, (2007) 13:116-121.

Nery et al., "Lesser Metatarsophalangeal Joint Instability: Prospective Evaluation and Repair of Plantar Plate and Capsular Insufficiency" Foot and Ankle International, Apr. 2012 vol. 33(4):301-311.

Weil, et al. "Anatomic Plantar Plate Repair Using the Weil Metatarsal Osteotomy Approach" Foot and Ankle Specialist, Jun. 22, 2011, 4:145-150. Originally published online on Mar. 18, 2011 http://fas.sagepub.com/content/4/3/145.

* cited by examiner

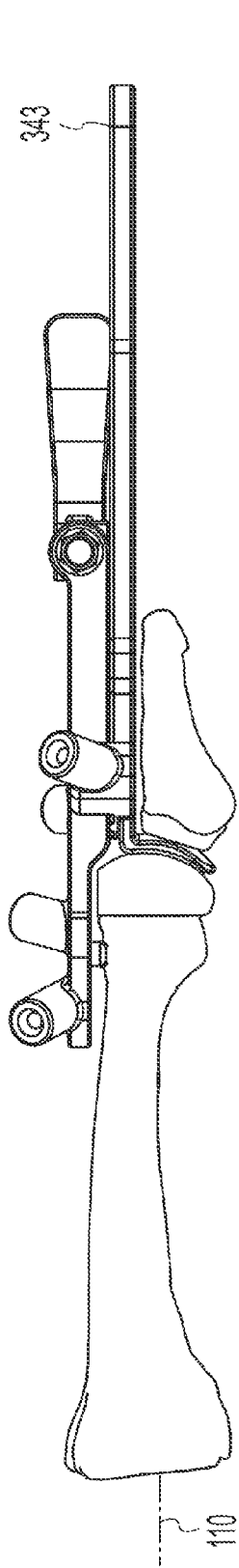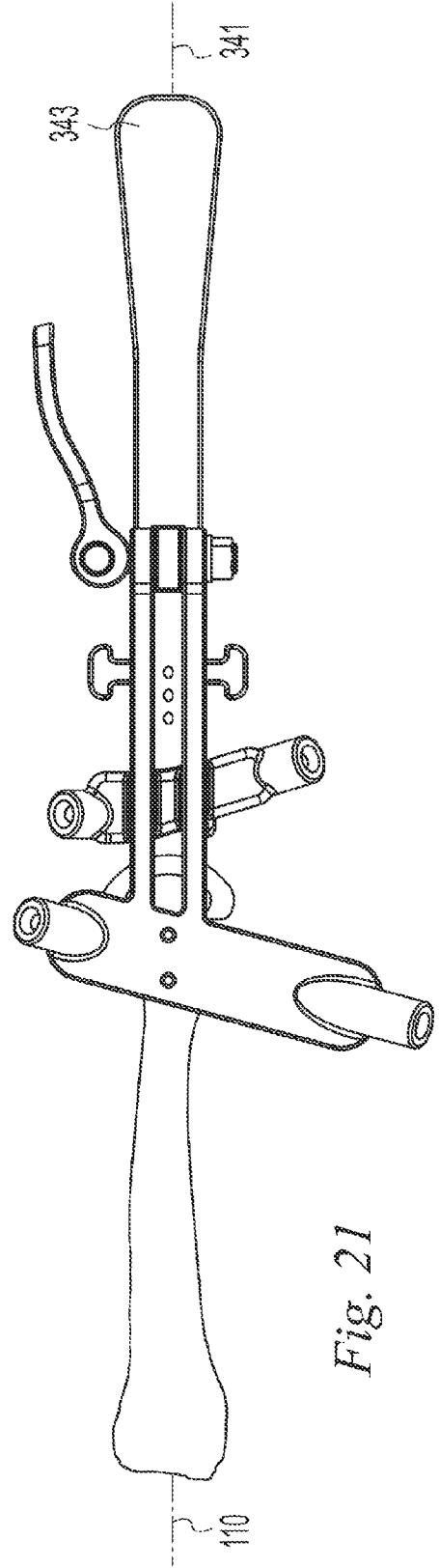
Fig. 20
Fig. 21

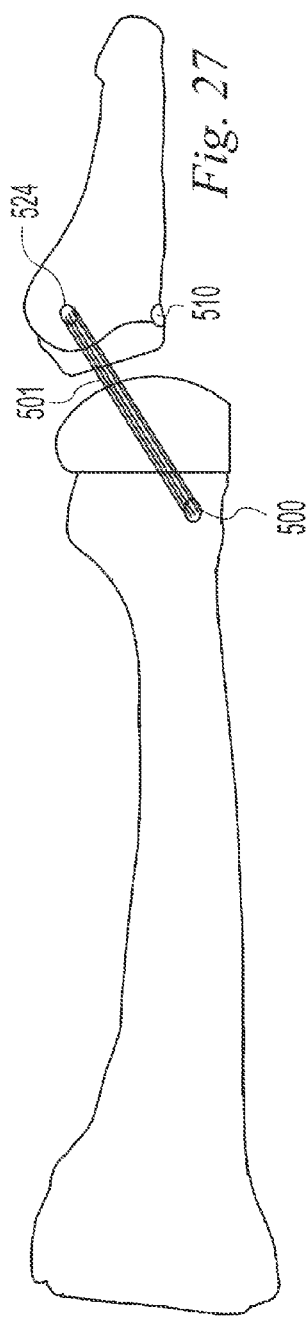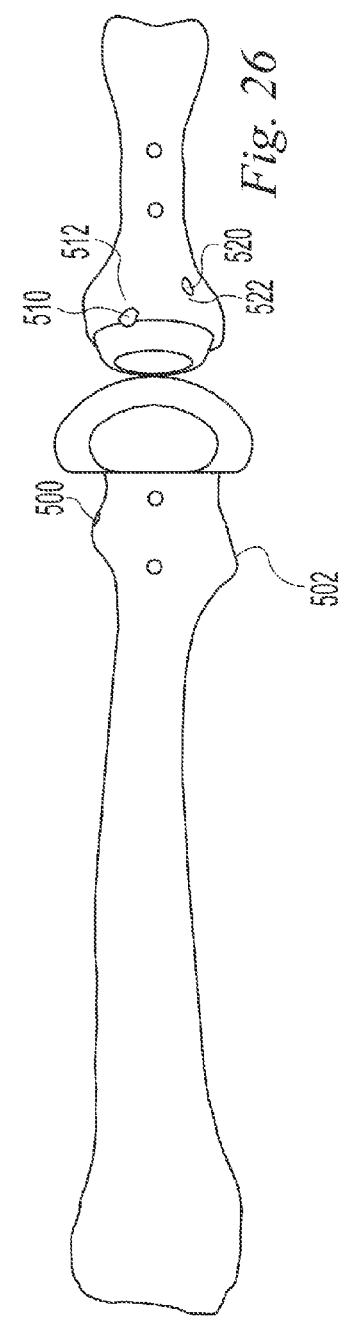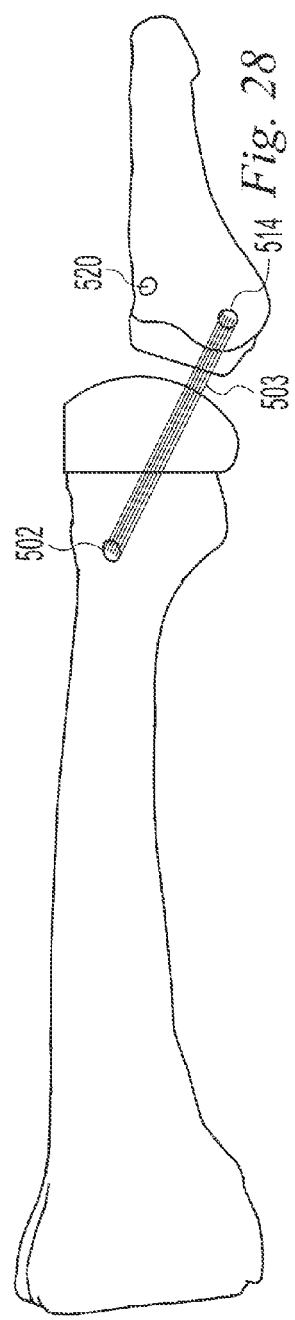

ORTHOPEDIC GUIDE AND METHOD

CROSS-REFERENCE TO RELATED APPLICATIONS

This application claims the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, U.S. Provisional Application No. 61/506,004, filed Jul. 8, 2011, all of which are herein incorporated by reference.

FIELD OF THE INVENTION

The invention relates to devices and methods suitable for cutting bones and in particular for forming holes in small bones adjacent a joint such as for example of the foot or hand.

BACKGROUND

Various conditions may affect skeletal joints such as the elongation or rupture of soft tissues, shortening or contracture of soft tissues, malformation of bones, and a variety of other conditions associated with the joint. Surgical intervention may be facilitated by cutting bones adjacent a joint. For example, holes may be formed in a bone in order to route and/or attach soft tissue, grafts, sutures, pins, screws, and for a variety of other purposes.

SUMMARY

The present invention provides a guide and method for cutting bones adjacent a joint at locations referenced to the joint anatomy.

In one aspect of the invention, a guide is registrable with the joint anatomy and has a guiding portion aligned to guide the formation of tunnels that intersect the anatomic insertions and/or origins of the soft tissues of the joint based on anthropometric data.

In another aspect of the invention, the guide includes one or more reference surfaces, edges, axes, or points that engage or are alignable relative to one or more anatomical landmarks of the joint. These landmarks relate to the kinematic operation of the joint. Anthropometric data may be utilized to locate a cutter guide so that it aligns with bone features related to the joint kinematics.

Bone cutters may include drills, pins, punches, broaches, saws, and other bone cutters. Bone cutting may include drilling, punching, broaching, slotting, sawing, slicing, and other cutting operations.

Guide reference surfaces may be flat, convex, concave, cylindrical, spherical, or any other suitable shape to engage or align relative to a landmark.

Anatomic landmarks may include an articular joint surface, a bone axis, an intramedullary canal, a joint plane, a body plane, a bone shaft, a condyle, an epicondyle, a ligament attachment, or any other suitable landmark that can be related to a desired cutter path.

Bone features may include an articular joint surface, a bone axis, an intramedullary canal, a joint plane, a body plane, a bone shaft, a condyle, an epicondyle, a ligament attachment, or any other suitable bone feature that is desired to be targeted.

The guiding portion may include a planar surface, notch, groove, hole, tube, rail, slot or other guiding portion able to guide a cutter in predetermined known relationship to the guide.

The position and orientation of an object in three dimensional space may be described relative to six degrees of freedom relative to three dimensional coordinate axes including three translational and three rotational degrees of freedom.

For example, in a guide configured for a metatarsophalangeal joint of the human foot, a concave reference surface may be registered with the convex head of the metatarsus by engaging the concave reference surface with the convex metatarsal head. If the reference surface is spherical it will engage the spherical metatarsal head to reference the joint center of rotation and eliminate all three translational degrees of freedom. The three rotational degrees of freedom may be resolved with additional landmarks. For example, by aligning a guide handle axis parallel to the axis of the metatarsus two degrees of rotational freedom are eliminated. The final degree of rotational freedom may be resolved, for example by aligning a guide surface, such as the guide handle top surface, parallel to the transverse plane.

In another example, the concave reference surface may be cylindrical. When it is engaged with the metatarsal head it will resolve two degrees of translational freedom. The third translational degree of freedom may be eliminated by aligning a center plane of the guide with the axis of the metatarsus. The rotational degrees of freedom may be eliminated as described above.

In another example, a convex reference surface may be registered to a concave landmark. For example, a convex reference surface may be registered with the articular surface of the proximal phalanx at the MTP joint.

There are many ways that the guide may be registered to a landmark. However, the guide may be designed using anthropometric data so that when it is registered relative to all six degrees of freedom, the guiding portion will guide a cutter to intersect a predetermined joint feature. For example, the guide may include a hole for guiding a drill to intersect the anatomic attachment of a ligament based on the guides relationship to anatomic landmarks. With the guide registered to multiple landmarks to fix its orientation relative to the surgical site in three dimensions, it is possible to target multiple bone features simultaneously.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 21 is a side elevation view of the guide of FIG. 5 in use with an MTP joint;

FIG. 26 is a dorsal view of the metatarsus and phalanx of the right second metatarsophalangeal joint of the human foot showing tunnels formed utilizing the guide of FIG. 5;

FIG. 27 is a medial view of the bones of FIG. 26;

FIG. 28 is a lateral view of the bones of FIG. 26; and

DESCRIPTION OF THE ILLUSTRATIVE EXAMPLES

The following illustrative examples illustrate instruments and techniques for treating skeletal joints. Instruments and techniques according to the present invention may be used in conjunction with any skeletal joint but the illustrative examples are shown in a size and form most suitable for the joints of the hand and foot. In particular, the illustrative examples depict their use on metatarsophalangeal (MTP) joints of the human foot. The illustrative instruments and techniques are also suitable for use on metacarpophalangeal (MCP) joints of the human hand.

Figure 1:
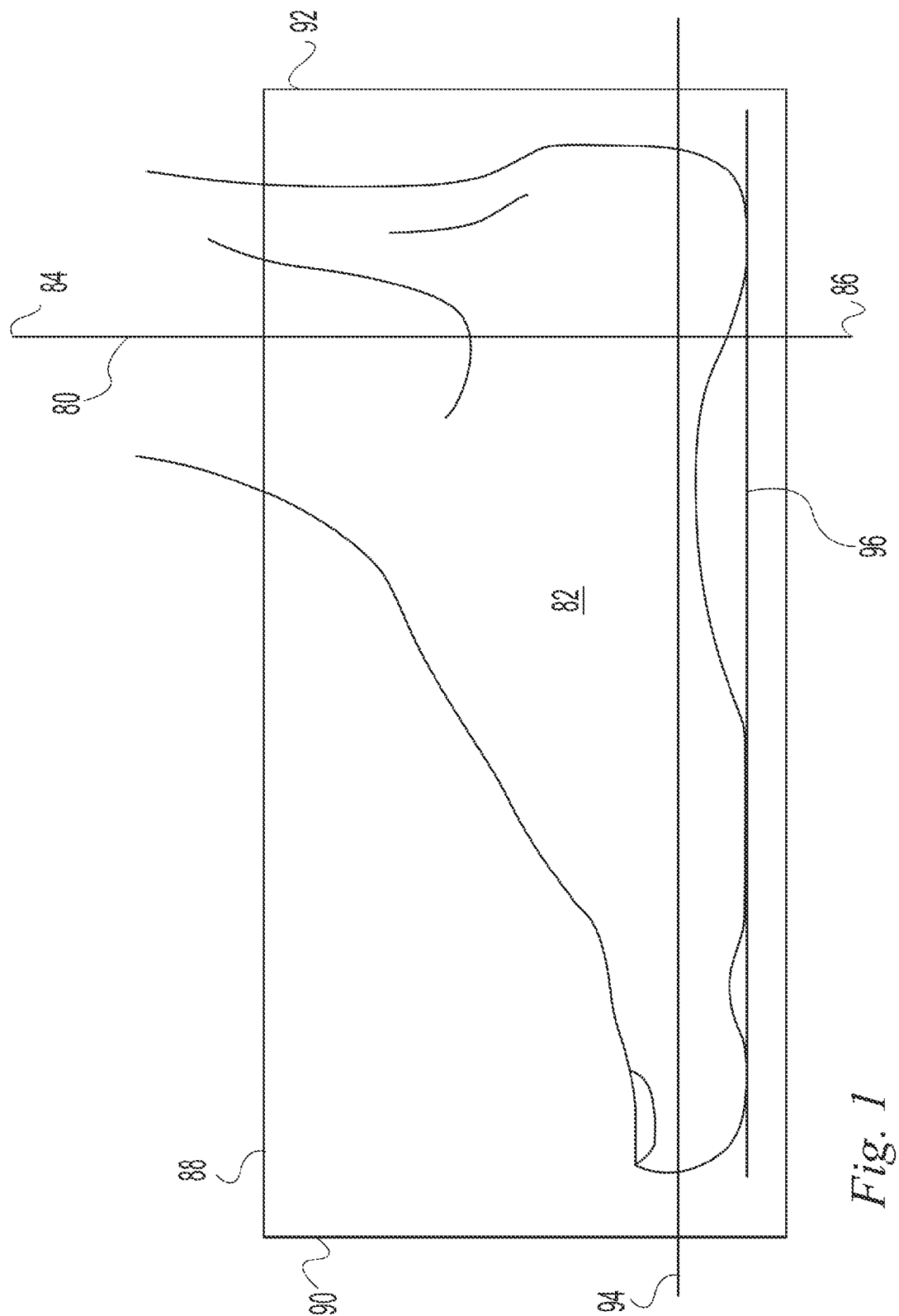
FIG. 1 is side elevation view of the human foot illustrating anatomic reference planes.

FIG. 1 illustrates the anatomic planes of the foot that are used for reference in this application. The coronal plane 80 extends from the medial aspect 82 to the lateral aspect of the foot and from dorsal 84 to plantar 86 and divides the foot between the toes and heel. The sagittal plane 88 extends anterior 90 to posterior 92 and dorsal 84 to plantar 86 and divides the foot into medial and lateral halves. The transverse plane 94 extends anterior 90 to posterior 92 and medial to lateral parallel to the floor 96.

Figure 3:
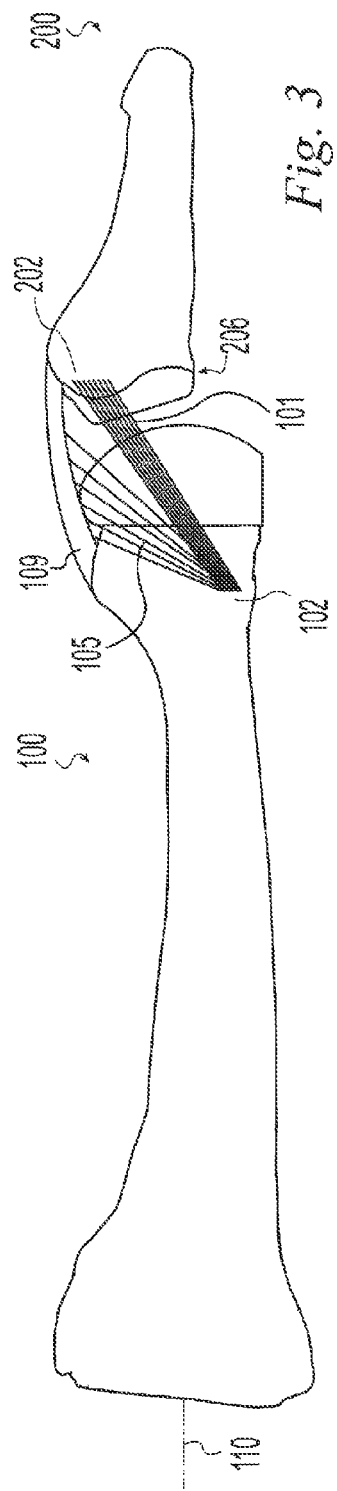
FIG. 3 is a medial view of the bones of FIG. 2.
Figure 2:
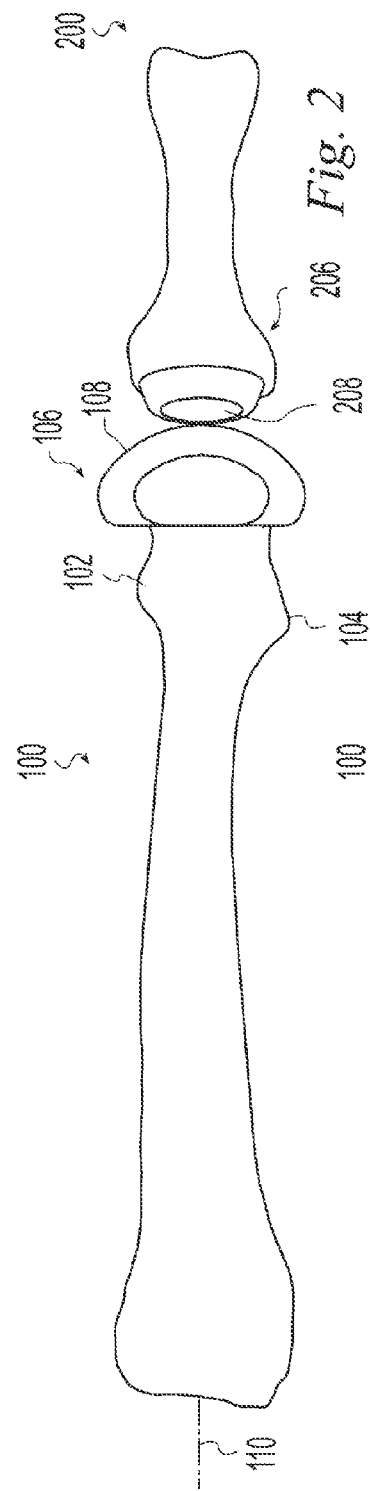
FIG. 2 is a dorsal view of the metatarsus and phalanx of the right second metatarsophalangeal joint of the human foot.
Figure 4:
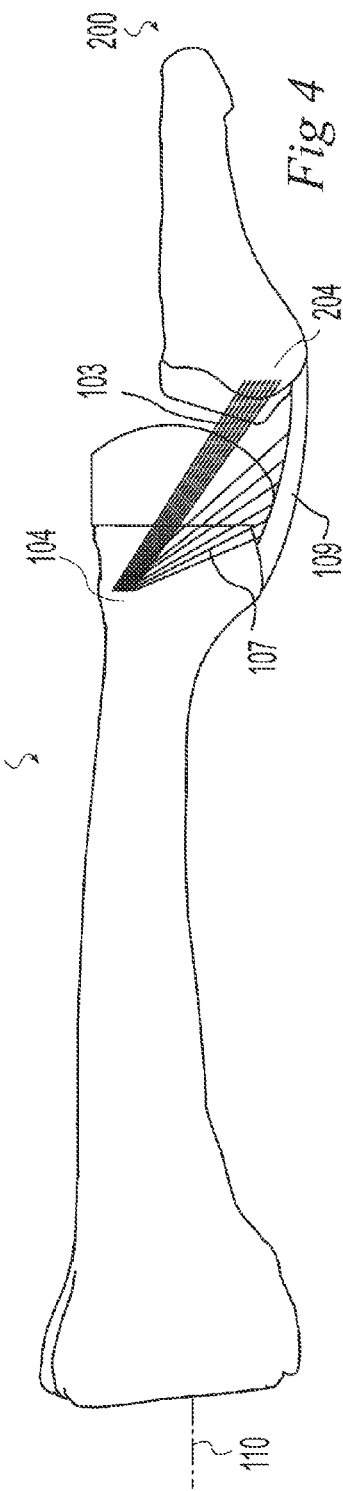
FIG. 4 is a lateral view of the bones of FIG. 2.
Figure 5:
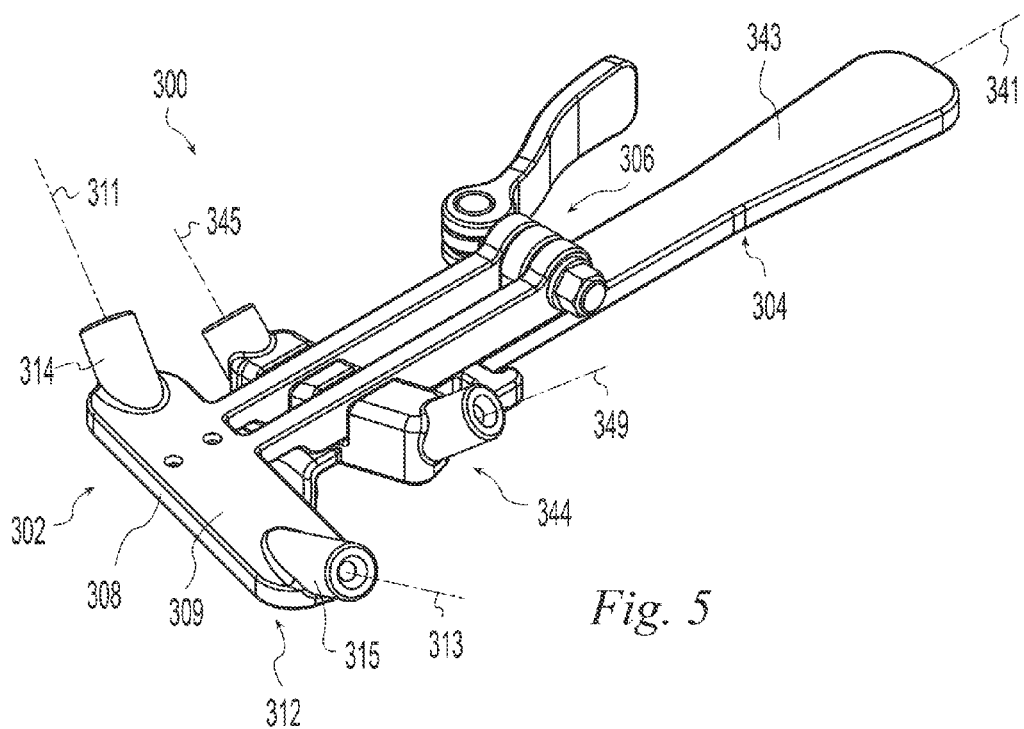
FIG. 5 is a perspective view of an illustrative example of a guide according to the present invention.
Figure 6:
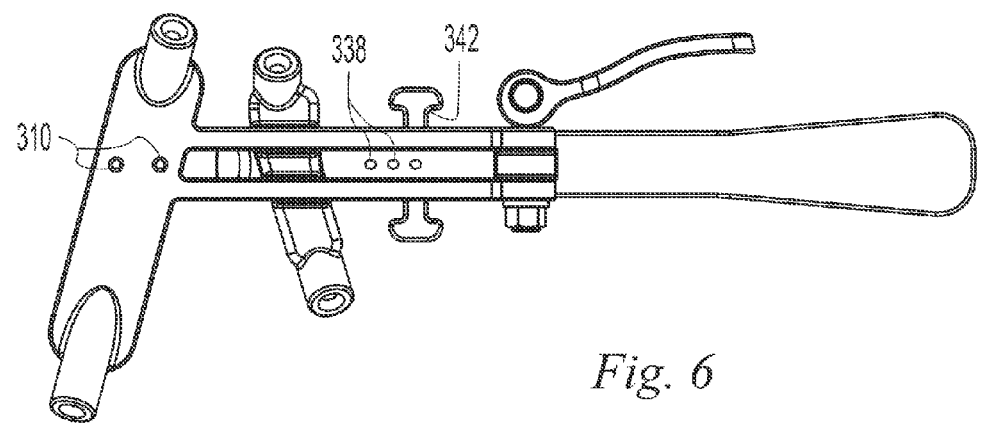
FIG. 6 is a top plan view of the guide of FIG. 5.
Figure 7:
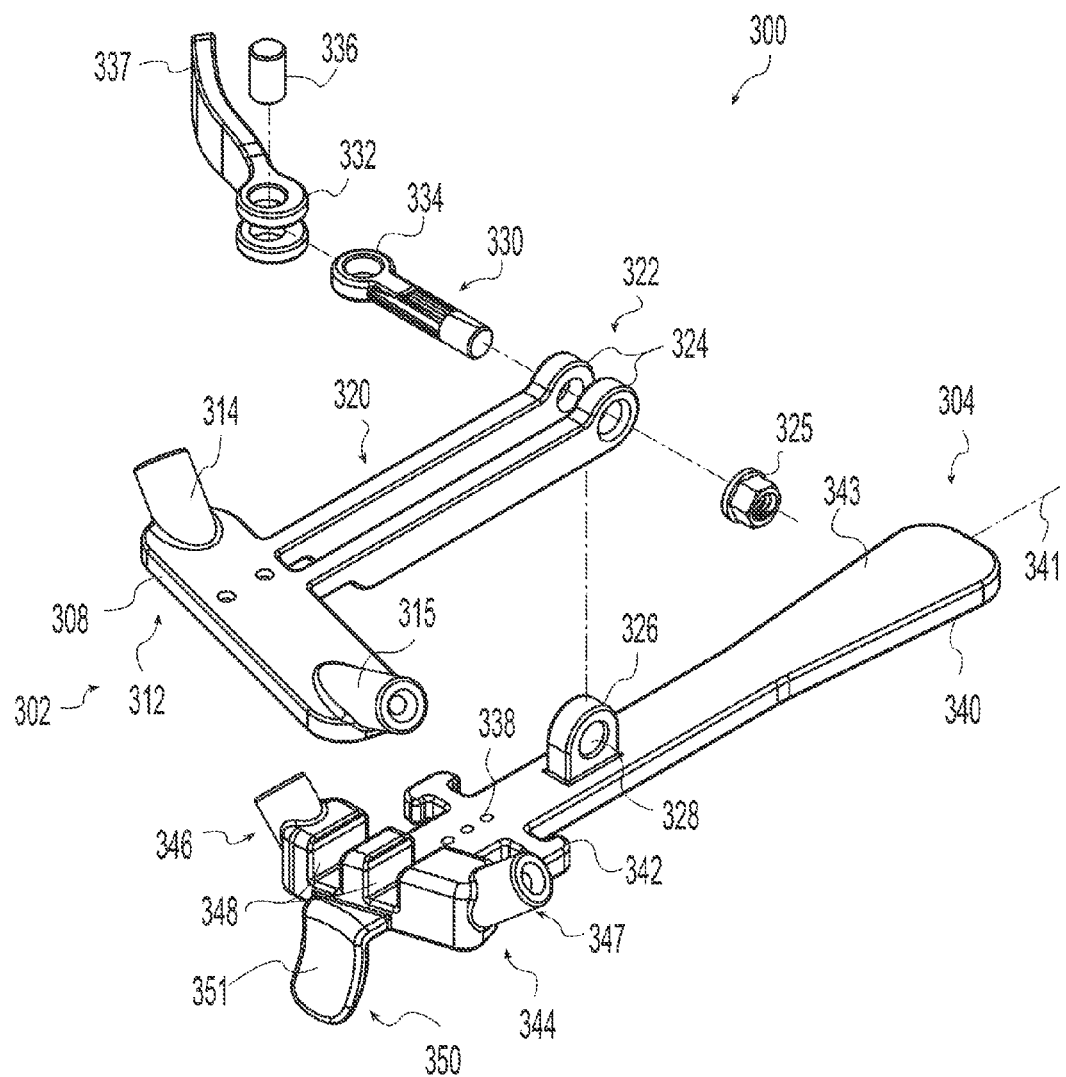
FIG. 7 is an exploded perspective view of the guide of FIG. 5.
Figure 8:
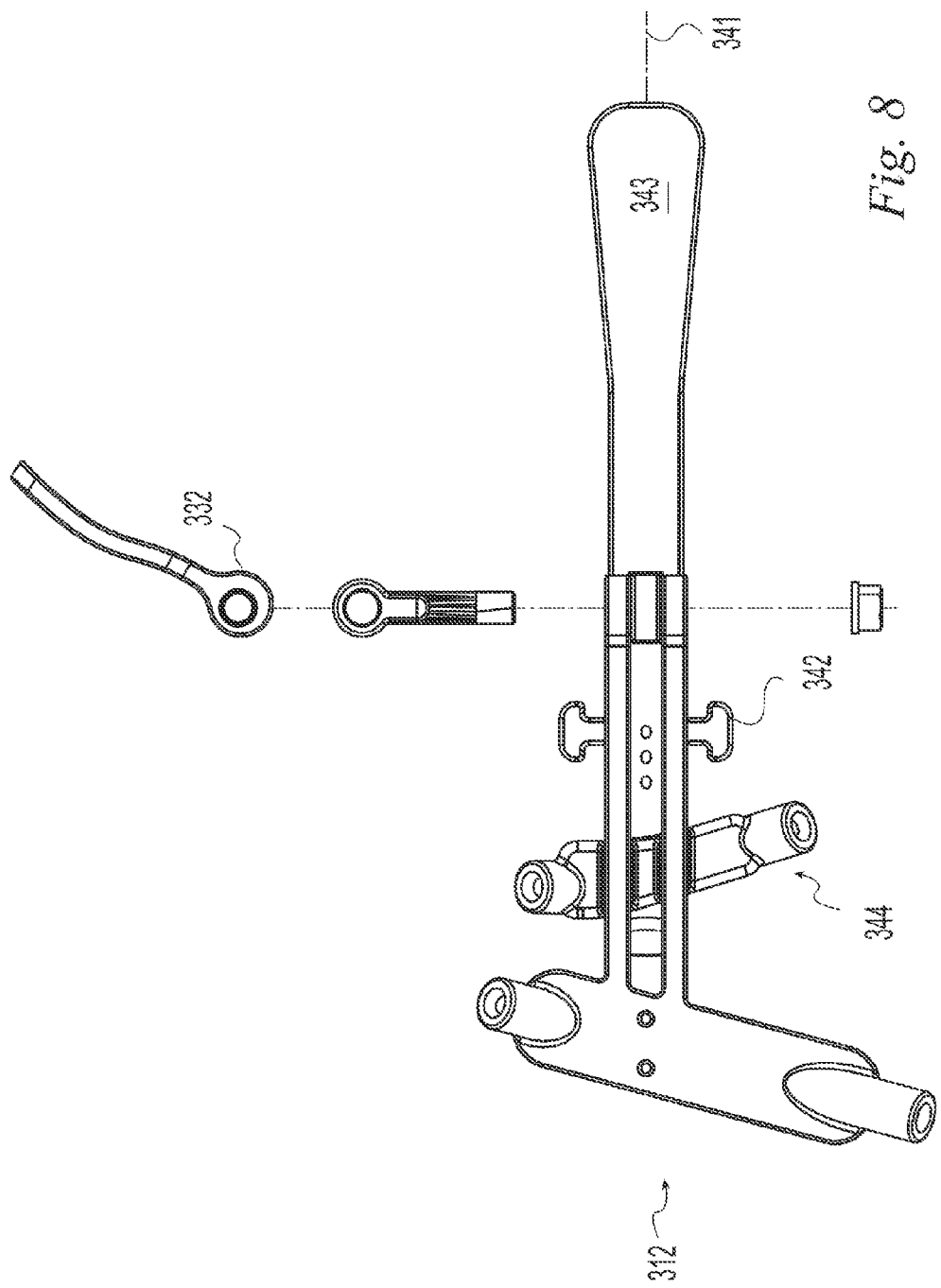
FIG. 8 is an exploded top plan view of the guide of FIG. 5.

FIGS. 2-4 illustrate the metatarsus 100 and proximal phalanx 200 of the second MTP joint of the right foot. The medial and lateral epicondyles 102, 104, located on the medial-dorsal and lateral-dorsal aspects of the metatarsus 100 respectively, are the origins of the medial and lateral proper collateral ligaments (PCLs) 101, 103 and the medial and lateral accessory collateral ligaments (ACLs) 105, 107 of the MTP joint. The medial PCL inserts at the medial-plantar aspect 202 and the lateral PCL inserts at the lateral-plantar aspect 204 of the phalanx 200. The ACLs fan out and insert into the plantar plate 109. The metatarsus includes a metatarsal head 106 having an articular surface 108 and the phalanx includes a phalangeal head 206 having an articular surface 208. The metatarsus 100 further includes a longitudinal axis 110 extending lengthwise down the center of the bone.

FIGS. 5-8 illustrate an exemplary guide 300 for guiding a cutter to cut a bone. In this illustrative example, the guide 300 is configured as a drill guide to guide a drill, punch, pin, broach or the like to form holes in the bones adjacent the second MTP joint of the right human foot. The drill guide 300 includes a pair of plate-like members 302, 304 joined at a hinge 306 allowing a single degree of freedom such that the members may be pivoted between a first position and a second position. The members include a plurality of fixation holes for receiving fixation devices, e.g. fixation pins or screws, to secure the members to underlying bones and guide holes to guide the formation of tunnels in the underlying bones to facilitate soft tissue repair, replacement, and/or augmentation around the joint. The first member 302 is configured to overlie the metatarsus and the second member 304 is configured to overly the phalanx.

The first member 302 includes a planar top surface 309, a first end 308 having fixation holes 310, and a metatarsal guide portion 312. The metatarsal guide portion 312 has a feature for guiding a cutter. In the illustrative example of FIGS. 4-7, the metatarsal guide portion 312 includes medial and lateral spaced apart, hollow, tubular extensions 314, 315 each projecting upwardly and outwardly from the top surface 309 and configured as a drill guide able to guide a drill, punch, broach, pin or the like. The tubular extensions 314, 315 are oriented so that their axes 311, 313 intersect below the metatarsal guide portion 312. A mounting yoke 320 having opposed spaced apart arms extends from the first end 308 to a second end 322 defining a pair of eyelets 324 which straddle a block 326 mounted on the second member 304. The block 326 has a hole 328 aligned with the eyelets 324. A bolt 330 and nut 325 join the eyelets 324 and block 326. A locking cam 332 is pinned to the head 334 of the bolt 330 for relative rotation about a pin 336 and includes a lever 337 extending from the cam for rotating the cam 332 between a locked and unlocked position. The bolt 330 and locking cam 332 are operable to press the eyelets 324 together against the block 326 to frictionally lock the members 302, 304 in relative angular relationship.

The second member 304 includes an elongated handle 340 having a longitudinal axis 341, a planar top surface 343, fixation holes 338 and a phalangeal guide portion 344. The phalangeal guide portion 344 has a feature for guiding a cutter. In the illustrative example of FIGS. 5-8, the phalangeal guide portion 344 includes medial and lateral spaced apart, hollow, tubular extensions 346, 347 each projecting upwardly and configured as a drill guide able to guide a drill, punch, broach, pin or the like along axes 345, 349. The phalangeal guide portion 344 includes a pair of grooves 348 for receiving the yoke 320 of the first member to increase the relative positional accuracy and stability of the members relative to one another when the members are locked in the second coaxial position. The second member 304 further includes a head referencing member 350 having a reference surface 351 for engaging an anatomic landmark. In the illustrative example of FIGS. 5-8, the head referencing member 350 has a concave spherical surface able to engage the articular surface of the metatarsal head. Opposite the concave surface is a convex back surface able to engage the articular surface of the phalangeal head. The second member further includes a pair of oppositely, laterally extending bosses 342 for receiving a band to secure the guide 300 to the phalanx.

Figure 9:
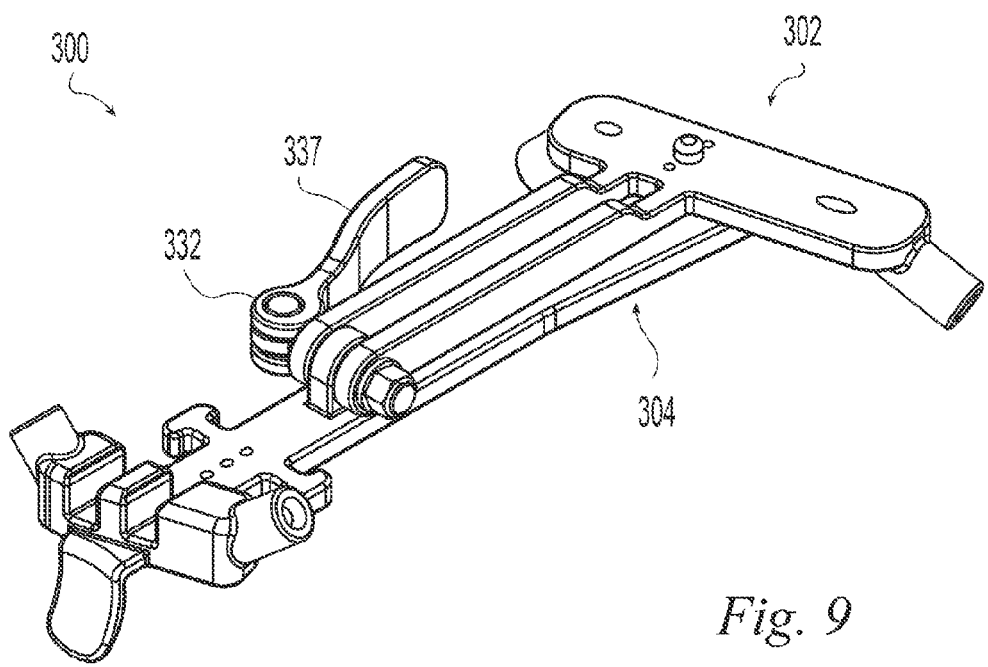
FIG. 9 is a perspective view of the guide of FIG. 5 showing a position of the guide.
Figure 10:
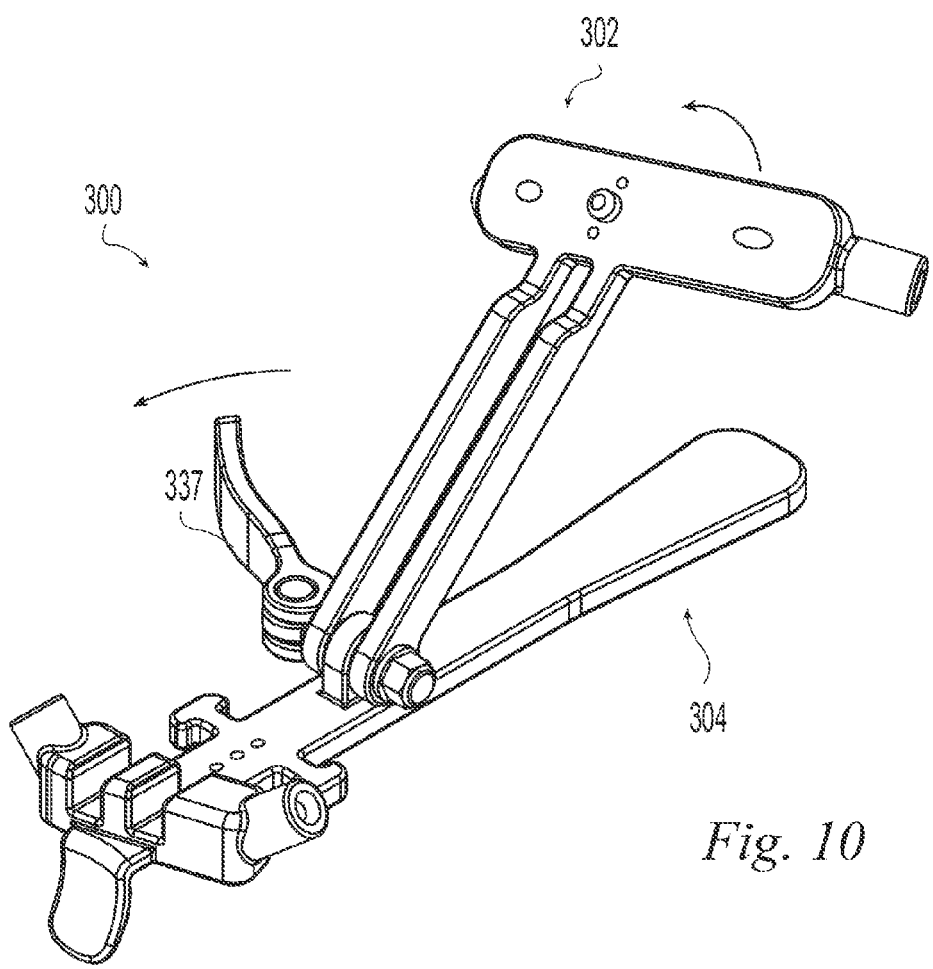
FIG. 10 is a perspective view of the guide of FIG. 5 showing a position of the guide.
Figure 11:
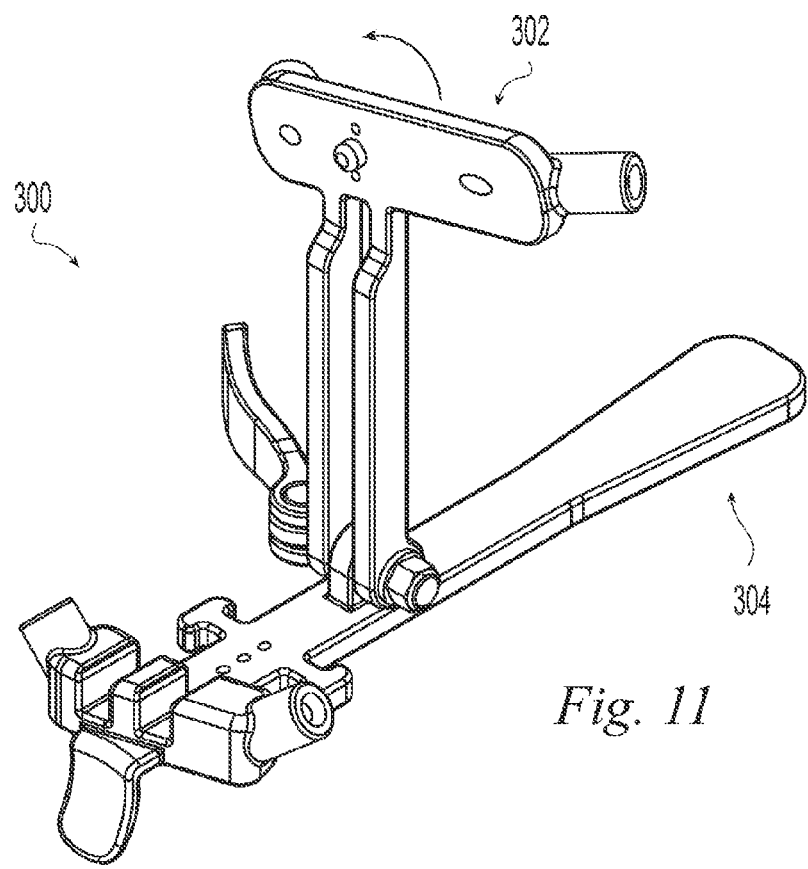
FIG. 11 is a perspective view of the guide of FIG. 5 showing a position of the guide.
Figure 12:
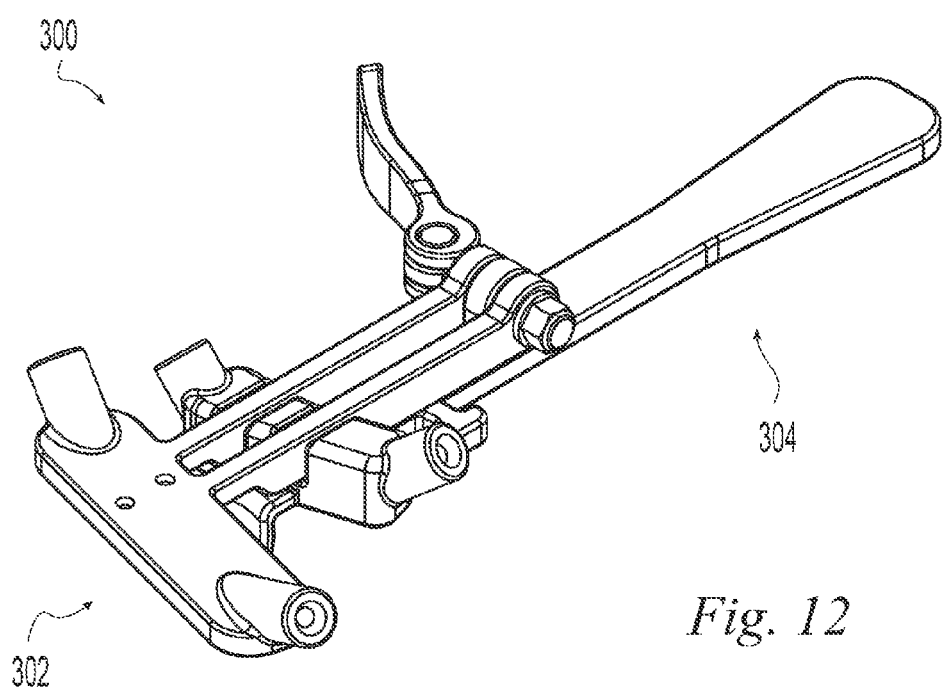
FIG. 12 is a perspective view of the guide of FIG. 5 showing a position of the guide.
Figure 13:
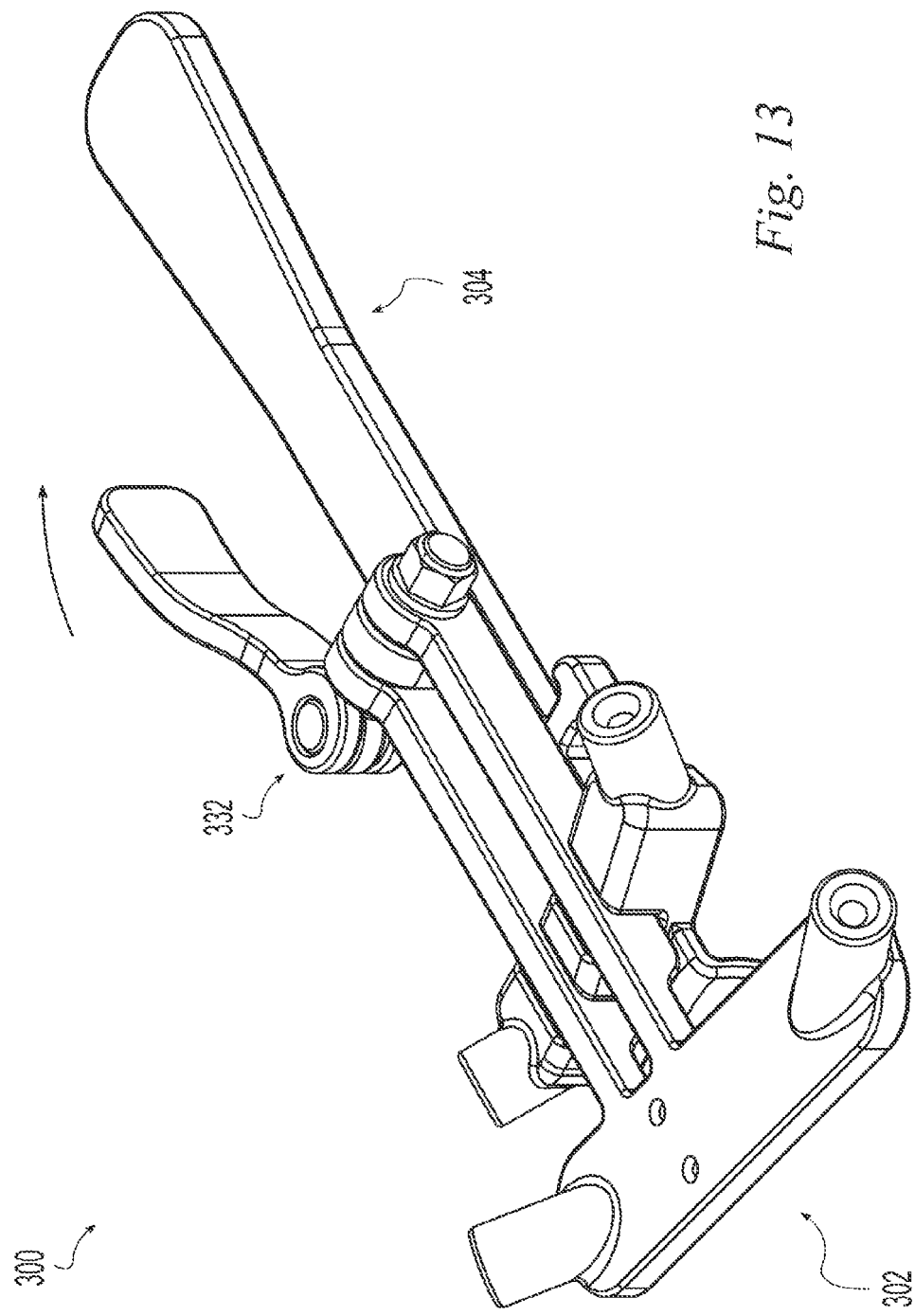
FIG. 13 is a perspective view of the guide of FIG. 5 showing a position of the guide.

FIG. 9 depicts the guide 300 locked in the first parallel position. FIG. 10 depicts the guide 300 with the cam 332 unlocked by rotating lever 337 and the first member 302 rotated part-way toward the second position. FIG. 11 depicts the guide 300 with the first member 302 rotated further toward the second position. FIG. 12 depicts the guide 300 with the first member rotated fully into the second position. FIG. 13 depicts the guide 300 with the cam 332 locked to fix the first and second members 302, 304 in the second position.

The relative position and orientation of the reference surface 351 of the head referencing member 350, the handle axis 341, the handle top surface 343, the phalangeal extensions 346, 347, and the metatarsal extensions 314, 315 are determined from averaged anthropometric data relating the metatarsal head articular surface, metatarsal longitudinal axis, and transverse plane of the human body to the medial and lateral PCL origins and insertions when the guide 300 is locked in the second position and placed on the bone with the reference surface 350 engaged with the metatarsal head 106, the handle axis 341 parallel to the axis 110 of the metatarsus, and the handle top surface 343 parallel to the transverse plane such that the metatarsal extension axes 311, 313 intersect the PCL origins and the phalangeal extension axes 345, 349 intersect the PCL origins.

Figure 14:
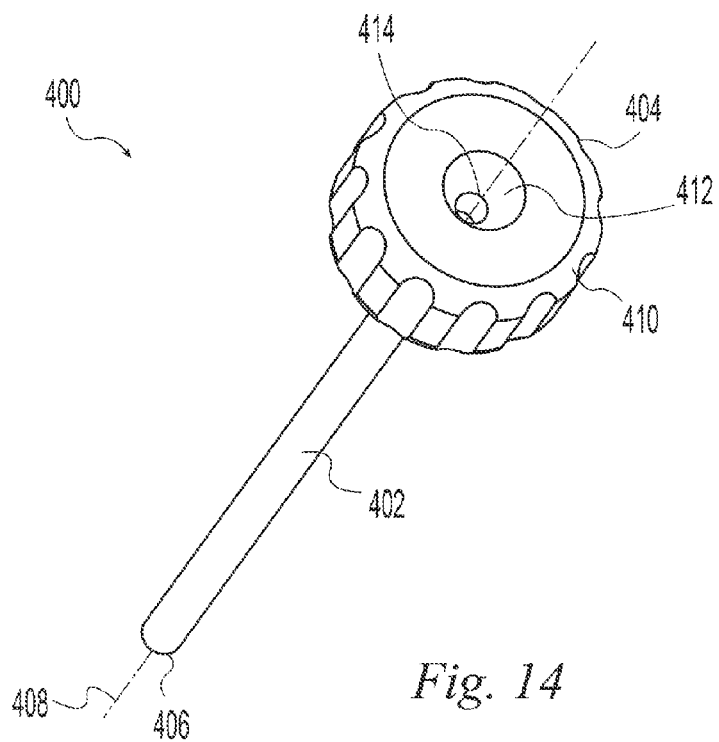
FIG. 14 is a perspective view of a tube useable with the guide of FIG. 5.
Figure 15:
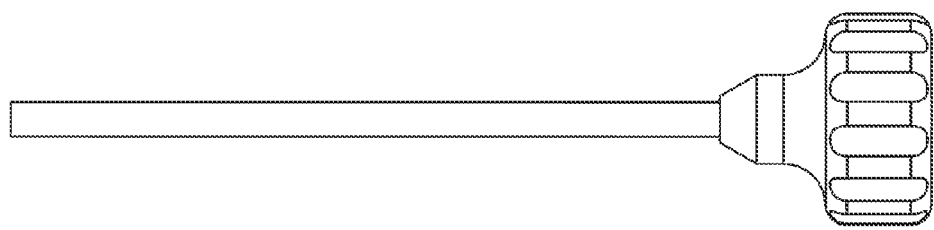
FIG. 15 is a side elevation view of the tube of FIG. 14.
Figure 16:
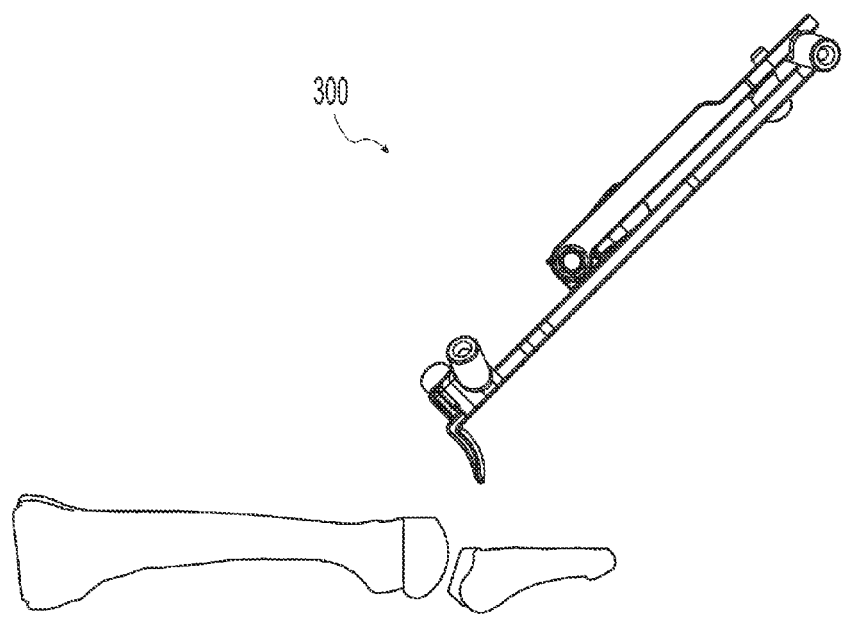
FIG. 16 is a side elevation view of the guide of FIG. 5 in use with an MTP joint.

FIGS. 14-15 illustrate an elongated tube 400 that may be used with guide 300 to protect soft tissue, facilitate engaging a cutter with the guide, and stabilize the cutter. For example, a long narrow drill, punch, pin, broach, or the like may be difficult to align with the extensions 314, 315, 346, 347 and/or may be so flexible that it tends to skive off the bone surface. The tube 400 includes a tubular shaft 402 having a proximal end 404, a distal end 406, and a longitudinal axis 408 extending from the proximal end 404 to the distal end 406. The proximal end is radially enlarged to form a knob 410. The knob 410 includes a counter sink 412 forming a funnel-like lead-in to the inner bore 414 of the tubular shaft 402. The outside of the shaft 402 is sized to slide into the extensions of the guide 300 and extend through the guide 300 to contact the underlying bone. The shaft 402 provides positive guidance of the cutter to the bone surface. The knob 410 provides the user with a gripping surface spaced away from the inner bore 414 to protect the user from being pricked by the cutter as the cutter is engaged with the inner bore 414. The countersink 412 guides the cutter into the inner bore 414.

Figure 17:
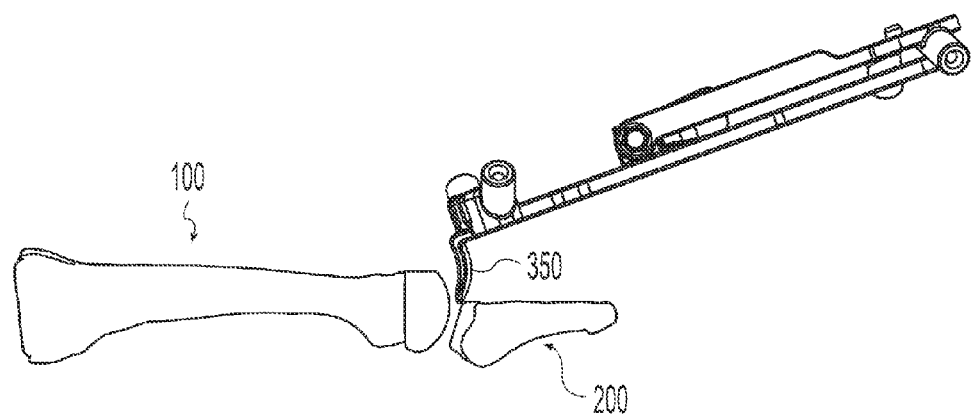
FIG. 17 is a side elevation view of the guide of FIG. 5 in use with an MTP joint.
Figure 18:
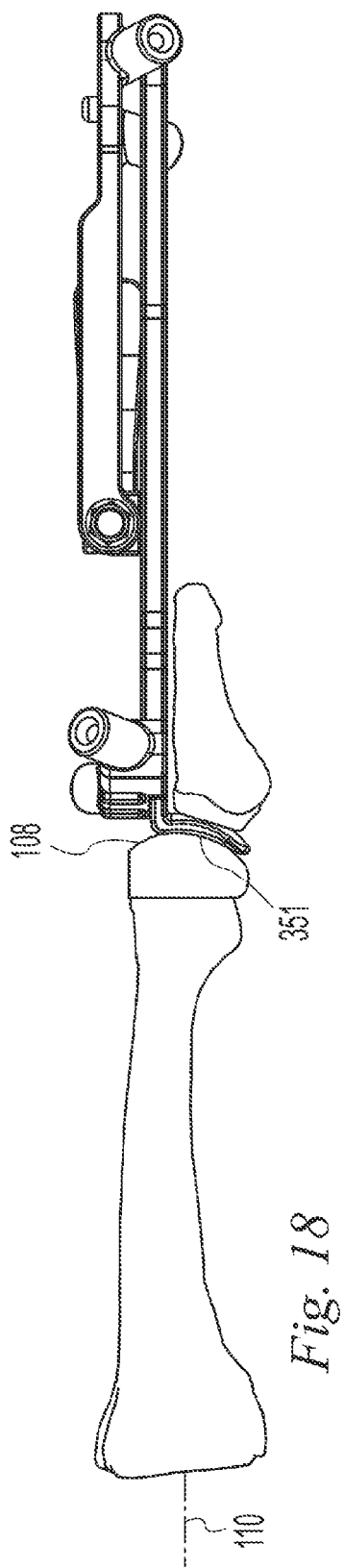
FIG. 18 is a side elevation view of the guide of FIG. 5 in use with an MTP joint.
Figure 19:
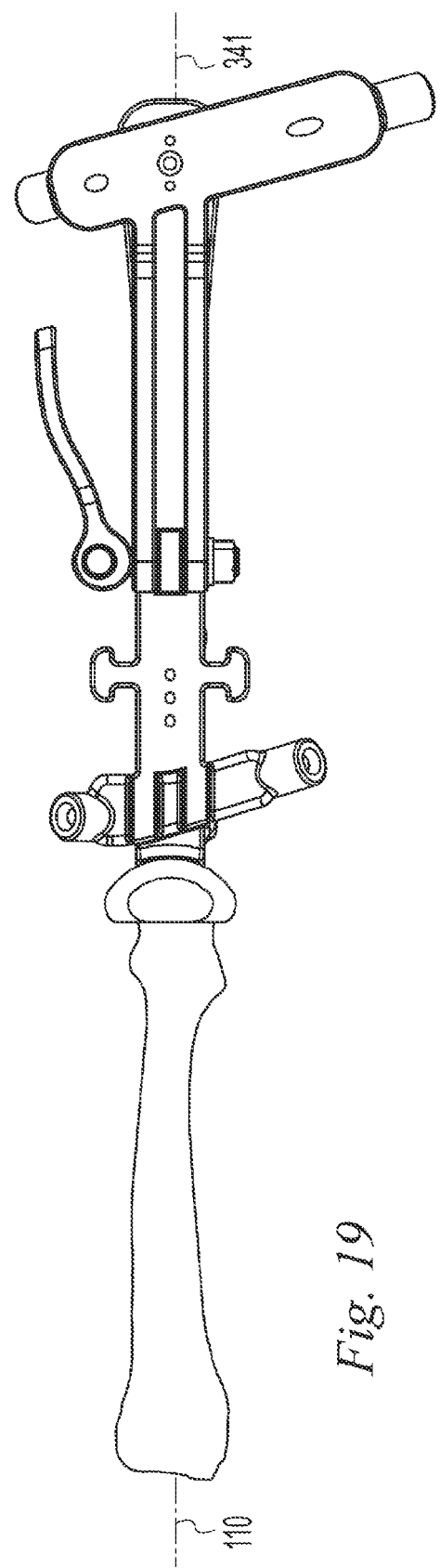
FIG. 19 is a top plan view of the guide of FIG. 5 in use with an MTP joint.
Figure 22:
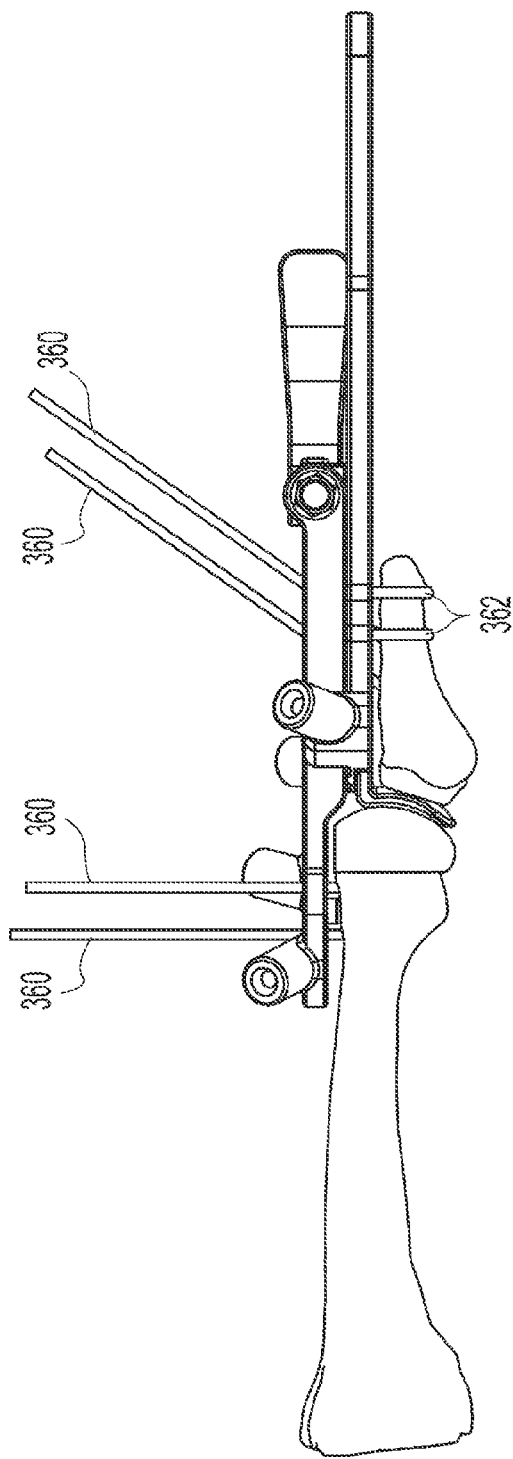
FIG. 22 is a top plan view of the guide of FIG. 5 in use with an MTP joint.
Figure 23:
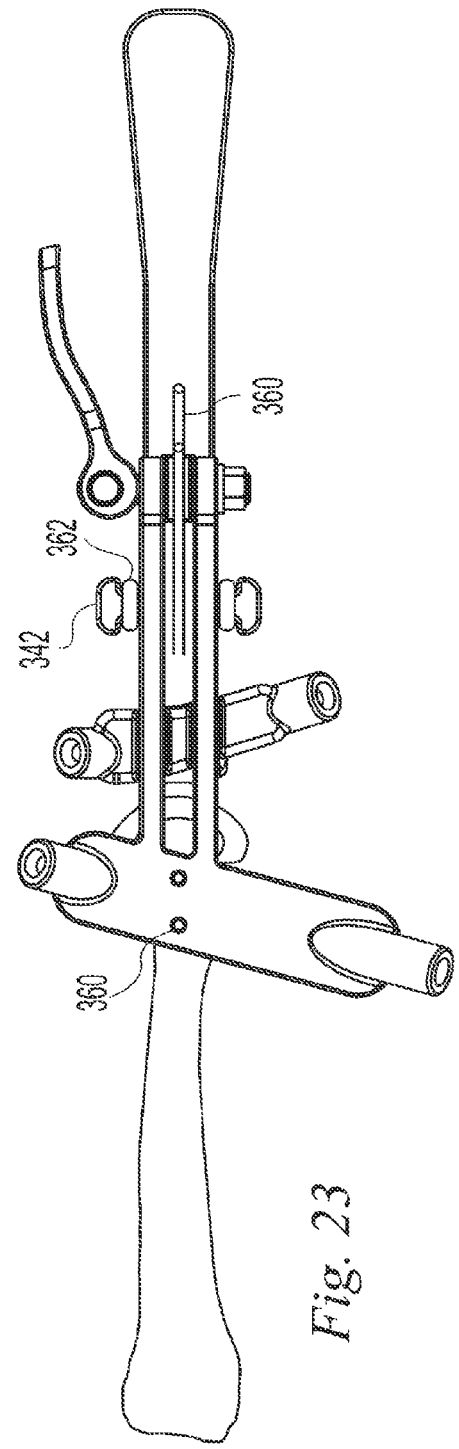
FIG. 23 is a side elevation view of the guide of FIG. 5 in use with an MTP joint.

FIGS. 16-25 illustrate the guide 300 in use to guide a cutter to form holes in the bones of the second MTP joint to facilitate, e.g., the reconstruction of the joint. The guide 300 is brought near the joint with the first and second members folded in the first position as shown in FIG. 15. The head referencing member 350 is inserted into the joint space between the metatarsus 100 and phalanx 200 as shown in FIG. 17. The concave reference surface 351 is registered with the convex articular surface 108 of the metatarsal head and the convex reference surface opposite the concave reference surface is registered with the concave articular surface of the proximal phalanx. The guide handle axis 341 is oriented parallel to the axis 110 of the metatarsus and the guide handle top surface 343 is oriented parallel to the transverse plane as shown in FIGS. 18 and 19. The first member is then pivoted into the second position as shown in FIGS. 20 and 21. The orientation of the guide 300 may be checked again. The cam is actuated to lock the members relative to one another and fixation devices, e.g. pins 360, may be placed in the guide fixation holes to fix the members to the bones as shown in FIGS. 22 and 23. An elastic band 362 may be wrapped around the phalanx and engaged with the bosses 342 to secure the second member 304 to the phalanx in addition to, or as an alternative to, the fixation pins 360.

Figure 24:
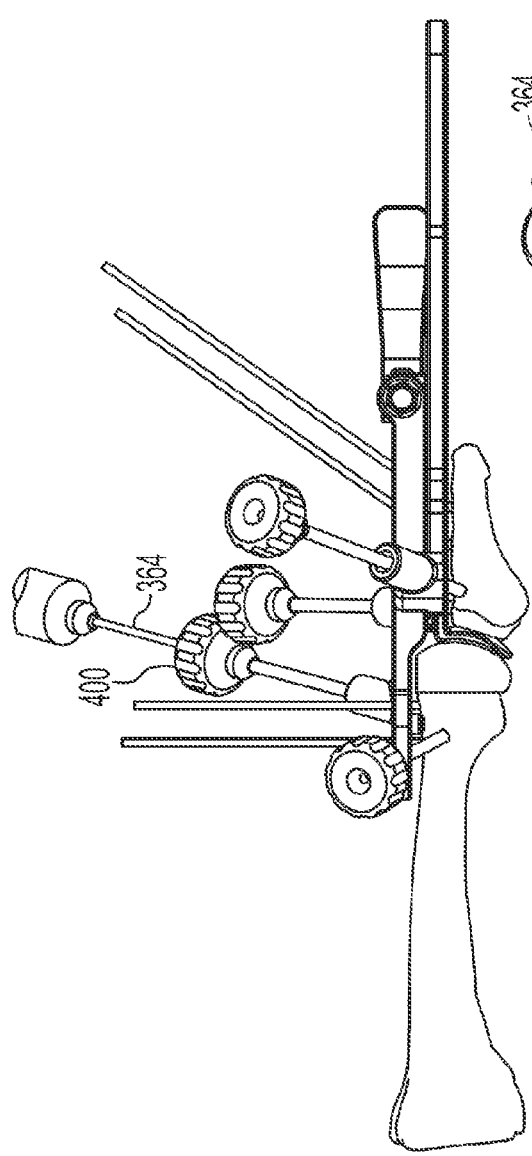
FIG. 24 is a top plan view of the guide of FIG. 5 in use with an MTP joint.
Figure 25:
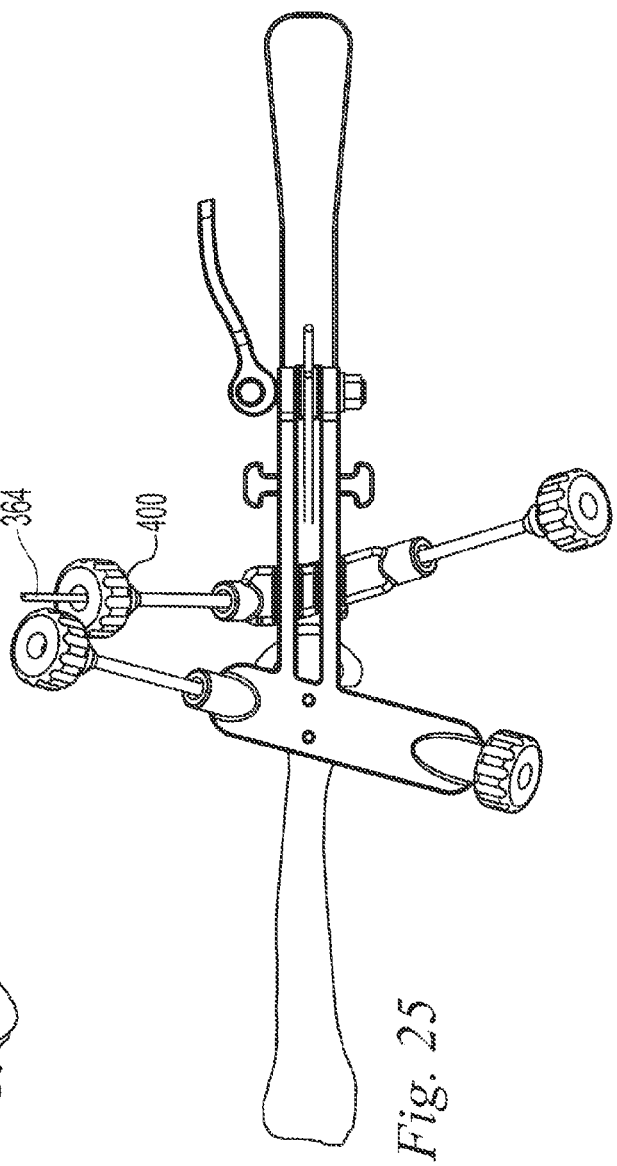
FIG. 25 is a side elevation view of the guide of FIG. 5 in use with an MTP joint.

Once the members are aligned and secured, the guide is used to guide a cutter to form one or more tunnels in the bones as shown in FIGS. 24 and 25. The cutter 364 may be engaged directly with an extension of a guide portion and advanced into the bone. Alternatively, an elongated tube 400 may first be engaged with the guide portion and extended to the bone surface. The cutter may then be engaged with the elongated tube 400 and advanced into the bone.

FIGS. 26-28 illustrate bone tunnels formed using guide 300 and ligaments reconstructed using the tunnels. The metatarsal guide portion 312 has guided a cutter to form a medial-dorsal tunnel 500 extending from the medial PCL origin into the metatarsus and a lateral-dorsal tunnel 502 extending from the lateral PCL origin into the metatarsus. The tubular extensions 314, 315 of the metatarsal guide portion 312 are oriented so that their axes intersect below the dorsal surface of the metatarsus. Thus, the tunnels 500, 502 intersect within the metatarsus and provide a path for fixing grafts 501, 503 to reconstruct one or both of the PCLs. A graft may be attached to the metatarsus by, e.g., pulling a traction suture through the tunnels and using it to pull the graft into the appropriate tunnel. For example, to attach a medial graft 501, the traction suture may be threaded into the medial tunnel 500 and out the lateral tunnel 502. The suture is then tensioned to draw the graft into the medial tunnel. The graft may be fixed by tying the suture, with a suture anchor, with an interference anchor, or with other suitable methods of fixation. A lateral graft 503 may be similarly positioned and both medial and lateral grafts may be simultaneously positioned.

The phalangeal guide portion 344 has guided a cutter to form a tunnel 510 extending from the medial-dorsal surface 512 of the phalanx to the insertion 514 of the lateral PCL on the lateral-plantar surface of the phalanx. The guide has also guided a cutter to form a tunnel 520 extending from the lateral-dorsal surface 522 of the phalanx to the insertion 524 of the medial PCL on the medial-plantar surface of the phalanx. These two phalangeal tunnels cross each other without intersecting. Grafts may be pulled into these tunnels by, e.g., passing a traction suture through one of the tunnels and drawing the graft into the tunnel. The holes 560 are formed by fixation members 360 used to hold the guide in place.

Figure 29:
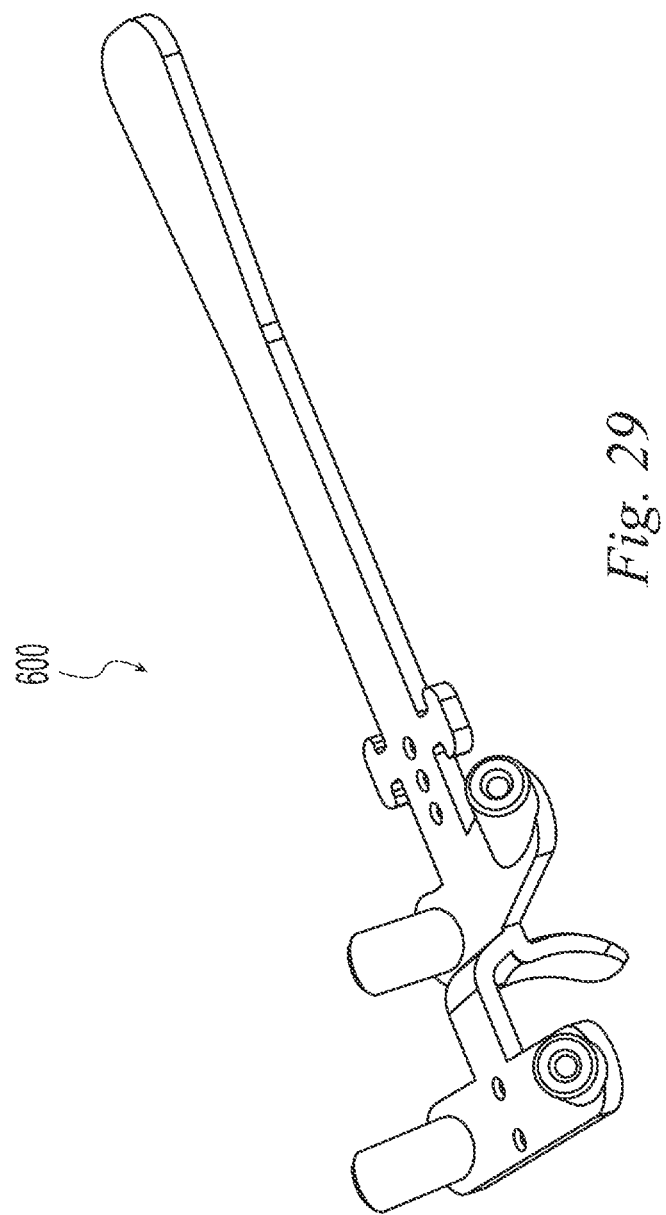
FIG. 29 is a perspective view of an illustrative example of a guide according to the present invention.

The illustrative guide of FIGS. 5-24 includes two separate members hinged together. Alternatively, the guide may be provided as two separate guides each having a joint reference surface and useable independently to drill tunnels in the metatarsus and proximal phalanx. Alternatively, the hinge may be removed and the two members combined into one non-movable unitary structure 600 as shown in FIG. 29.

The illustrative guide of FIGS. 5-24 is configured to reference to the anatomy of the right second MTP joint of the human foot to guide a cutter to form tunnels in the metatarsus and phalanx that intersect the medial and lateral PCL origins and insertions to facilitate routing and attaching ligaments to reconstruct the PCLs. The guide may be mirrored for use on the left foot and the guide may be provided in sizes for different MTP joints and various sized feet. However, it has been found that the variation of the PCL origin and insertion anatomy is surprisingly small for the second MTP joint across a wide range of foot sizes and it is possible to provide a single sized guide for all left second MTP joints and another for all right MTP joints for feet from at least a woman's US size 7 to a man's US size 11.

The medial and lateral ACLs of the MTP joint have origins that are co-located with the medial and lateral PCL origins on the metatarsus. The ACLs then fan out to insert into the plantar plate close to where the plantar plate transitions into the intermetatarsal ligament (IML). Therefore, the same tunnels used to reconstruct the PCL origins may be used to reconstruct the ACL origins such that the illustrative guide 300 configured for PCL reconstruction may also be used for ACL reconstruction.

The drill guide may have any number of cutter guides targeted at any desired anatomical feature. While the illustrative embodiment has depicted a guide configured for ACL and PCL reconstruction of the right human MTP joint, the guide may be similarly configured to target other ligament reconstructions or other surgical procedures at other locations throughout the body.

What is claimed is:

1. A bone drill guide useable near a metatarsal phalangeal (MTP) joint of a human foot to guide the formation of a hole in a bone that intersects a ligament boney attachment adjacent the joint, the MTP joint including a metatarsal bone having a longitudinal axis and a head with an articular surface, and a phalangeal bone having a head with an articular surface, the bone drill guide comprising:
   a body having a first reference portion engageable with at least one articular surface of the MTP joint and a first drill guiding portion, the first drill guiding portion being oriented relative to the first reference portion based on human anatomy relating the location of a first ligament boney attachment to at least one articular surface of the MTP joint, the guide being operable to engage the first reference portion with at least one articular surface of the MTP joint to position the first drill guiding portion in alignment with the boney attachment of the first ligament, wherein the first reference portion comprises a member extending away from the body and having a concave surface engageable with the metatarsal head.

2. The bone drill guide of claim 1 wherein the concave surface is spherical and engageable with the metatarsal head, the spherical engagement operable to constrain the guide in three translational degrees of freedom.

3. The bone drill guide of claim 2 wherein the body comprises a guide longitudinal axis and a planar portion, the guide being operable, while the concave surface is engaged with the metatarsal head, to align the guide longitudinal axis parallel to the longitudinal axis of the metatarsal bone to eliminate two degrees of rotational freedom and to align the planar portion parallel to the transverse plane of the foot to eliminate a third degree of rotational freedom.

4. The bone drill guide of claim 1 wherein the concave surface is cylindrical and engageable with the metatarsal head, the cylindrical engagement operable to constrain the guide in two translational degrees of freedom.

5. The bone drill guide of claim 4 wherein the body comprises a guide longitudinal axis and a planar portion, the guide being operable, while the concave surface is engaged with the metatarsal head, to align the guide longitudinal axis with the longitudinal axis of the metatarsal bone to eliminate one degree of translational freedom and two degrees of rotational freedom and to align the planar portion parallel to the transverse plane of the foot to eliminate a third degree of rotational freedom.

6. A bone drill guide useable near a metatarsal phalangeal (MTP) joint of a human foot to guide the formation of a hole in a bone that intersects a ligament boney attachment adjacent the joint, the MTP joint including a metatarsal bone having a longitudinal axis and a head with an articular surface, and a phalangeal bone having a head with an articular surface, the bone drill guide comprising:
   a body having a first reference portion engageable with at least one articular surface of the MTP joint and a first drill guiding portion, the first drill guiding portion being oriented relative to the first reference portion based on human anatomy relating the location of a first ligament boney attachment to at least one articular surface of the MTP joint, the guide being operable to engage the first reference portion with at least one articular surface of the MTP joint to position the first drill guiding portion in alignment with the boney attachment of the first ligament, wherein the body comprises first and second rigid members joined together at a hinge in relative rotating relationship and the first drill guiding portion includes a hole defining a first drill guiding axis through the first rigid member alignable with the boney attachment of a ligament to the metatarsal bone.

7. The bone drill guide of claim 6 wherein the second rigid member includes a second drill guiding portion having a hole defining a second drill guiding axis simultaneously alignable with the boney attachment of a ligament to the phalangeal bone.

8. The bone drill guide of claim 7 wherein the first and second rigid members further include holes for receiving fixation members to attach the rigid members to the metatarsal and phalangeal bones.

9. A method of drilling a tunnel in a bone of a metatarsal phalangeal (MTP) joint of a human foot that intersects a ligament boney attachment adjacent the joint, the MTP joint including a metatarsal bone having a longitudinal axis and a head with an articular surface, and a phalangeal bone having a head with an articular surface, the method comprising:
   positioning a drill guide adjacent the MTP joint, the drill guide comprising a body having a first reference portion engageable with at least one articular surface of the MTP joint and a first drill guiding portion;
   engaging the first reference portion with at least one articular surface of the MTP joint to position the first drill guiding portion in alignment with the first ligament boney attachment; guiding a drill with the first drill guiding portion to form a bone tunnel, wherein the first reference portion comprises a member extending outwardly from the body and having a concave surface and engaging the first reference portion comprises engaging the concave surface with the metatarsal head.

10. The method of claim 9 wherein the concave surface is spherical and engaging the concave surface with the metatarsal head constrains the guide in three translational degrees of freedom.

11. The method of claim 10 wherein the body further comprises a guide longitudinal axis and a planar portion, the method further comprising:
   aligning the guide longitudinal axis parallel to the longitudinal axis of the metatarsal bone to eliminate two degrees of rotational freedom; and
   aligning the planar portion parallel to the transverse plane of the foot to eliminate a third degree of rotational freedom.

12. The method of claim 9 wherein the concave surface is cylindrical and engaging the concave surface with the metatarsal head constrains the guide in two translational degrees of freedom.

13. The method of claim 12 wherein the body further comprises a guide longitudinal axis and a planar portion, the method further comprising:
   aligning the guide longitudinal axis with the longitudinal axis of the metatarsal bone to eliminate one degree of translational freedom and two degrees of rotational freedom; and
   aligning the planar portion parallel to the transverse plane of the foot to eliminate a third degree of rotational freedom.

14. A method of drilling a tunnel in a bone of a metatarsal phalangeal (MTP) joint of a human foot that intersects a ligament boney attachment adjacent the joint, the MTP joint including a metatarsal bone having a longitudinal axis and a head with an articular surface, and a phalangeal bone having a head with an articular surface, the method comprising:

positioning a drill guide adjacent the MTP joint, the drill guide comprising a body having a first reference portion engageable with at least one articular surface of the MTP joint and a first drill guiding portion;

engaging the first reference portion with at least one articular surface of the MTP joint to position the first drill guiding portion in alignment with the first ligament boney attachment; guiding a drill with the first drill guiding portion to form a bone tunnel, wherein the body comprises first and second rigid members joined together at a hinge in relative rotating relationship and the first rigid member includes the first drill guiding portion having a hole defining a first drill guiding axis and the second rigid member includes a second drill guiding portion having a hole defining a second drill guiding axis; further wherein the steps of positioning the drill guide adjacent the joint and engaging the first reference portion with the MTP joint are accomplished with the second rigid member overlying the first rigid member, the method further comprising;

positioning the first and second rigid members over the phalangeal bone of the MTP joint;

rotating the first rigid member relative to the second rigid member to position the first rigid member over the metatarsal bone of the MTP joint;

securing the first rigid member to the metatarsal bone; and securing the second rigid member to the phalangeal bone.

* * * * *